United States Patent [19]

Manassen et al.

[11] 4,415,500

[45] Nov. 15, 1983

[54] CATALYST COMPRISING A COMPLEX OF AN ELONGATED ORGANIC MOIETY AND A METAL ION

[75] Inventors: Joost Manassen, Rehovot; Yaakov Dror, Tel Aviv, both of Israel

[73] Assignee: Yeda Research and Development Company Ltd., Rehovot, Israel

[21] Appl. No.: 240,116

[22] Filed: Mar. 3, 1981

[30] Foreign Application Priority Data

Mar. 14, 1980 [IL] Israel ................................. 59647

[51] Int. Cl.$^3$ ............................................. C07F 15/00
[52] U.S. Cl. .............................. 260/429 R; 502/155; 502/167; 502/170
[58] Field of Search ...................... 260/429 R, 439 R; 252/431 C, 431 P

[56] References Cited

U.S. PATENT DOCUMENTS

| | | | |
|---|---|---|---|
| 3,939,188 | 2/1976 | McVicker | 260/429 R |
| 4,070,403 | 1/1978 | Homeier et al. | 568/454 |
| 4,173,575 | 11/1979 | Carlock | 260/429 R |
| 4,201,714 | 5/1980 | Hughes | 260/429 R X |
| 4,215,066 | 7/1980 | Kalck et al. | 260/429 R |
| 4,265,827 | 5/1981 | Knowles et al. | 260/429 R X |
| 4,277,414 | 7/1981 | Saito et al. | 260/429 R |
| 4,288,380 | 9/1981 | Billig et al. | 260/429 R |
| 4,294,989 | 10/1981 | Knowles et al. | 260/429 R X |
| 4,298,541 | 11/1981 | Oswald | 260/429 R |
| 4,306,082 | 12/1981 | Brunner et al. | 260/429 R X |
| 4,315,867 | 2/1982 | Hänssle | 260/439 R |
| 4,328,163 | 5/1982 | Hänssle | 260/439 R |

*Primary Examiner*—Helen M. S. Sneed
*Attorney, Agent, or Firm*—Browdy and Neimark

[57] ABSTRACT

A catalyst for use in homogeneous catalysis comprises a backbone of at least 5 carbon atoms chain length, which may comprise aromatic moieties and also hetero atoms, a polar moiety at one of the ends of the backbone and a ligand moiety at its other end, such ligand moiety being adapted to form a complex with a metal ion. A process of hydrogenation or of hydroformylation comprises contacting an aqueous phase containing a catalyst as defined above, with an organic phase comprising the reactant, introducing hydrogen or a hydrogen-carbon monoxide mixture with agitation until the reaction is terminated, separating the phases and recovering the desired reaction products from the organic phase.

5 Claims, No Drawings

CATALYST COMPRISING A COMPLEX OF AN ELONGATED ORGANIC MOIETY AND A METAL ION

FIELD OF THE INVENTION

The present invention relates to a novel kind of catalyst for use at the interface of two phases. The novel catalyst is soluble in an aqueous phase and as it comprises a suitable ligand at one end of the molecule, which ligand is adapted to exert a catalytic activity on reactants in the other, organic phase. The invention further relates to reactions and chemical processes effected by means of such novel catalysts.

BACKGROUND OF THE INVENTION

Several types of catalytic reaction in two-phase systems are known. One of these is termed phase-transfer catalysis, Dehmlow Angew.Chemie (Eng Ed.) 16,493 (1977) where the reaction takes place in the organic phase by the use of two large organic cations, and where the leaving group enters the aqueous phase. Another system is that of micellar catalysis, Fendler et al, Catalysis in Micellar and macromolecular systems, Academic Press, New York, 1975. The reaction is effected in a micellar system obtained from an organic and an aqueous phase in conjunction with a surface active agent. A highly polar layer is formed at the interphase and this may stabilize the transition state of the reaction. In another system catalytic reactions are effected in a system comprising sulfonated triphenyl phosphine, which serves as catalyst in the aqueous phase, see French patent application No. 2314910.

SUMMARY OF THE INVENTION

According to the present invention there is provided a novel catalyst which is active at the interface of two liquid phases, one organic and the other aqueous, the polar part of the catalyst molecule being within the aqueous phase, while the other end of the said molecule is in the organic phase, said other end carrying a ligand complexed with a catalytically active metal. The novel catalyst can be used repeatedly without any significant loss of catalyst. According to a preferred embodiment of the invention the catalyst is a molecule comprising an elongated organic moiety which carries at its one end a ligand adapted to complex a catalytically active metal cation, while the other end of the molecule is of polar nature, resulting in the dissolution of the polar part in the aqueous phase. Due to the ligand carrying the cation, the part of the catalyst molecule extending into the organic phase is adapted to catalyze certain reactions, and at the completion of the reaction the two phases are separated, the catalyst stays in the aqueous phase, and this can be contacted with a fresh quantity of organic phase and reactants to effect further reactions. The reaction is advantageously effected under adequate agitation resulting in an increase of the interface of the phases. Sometimes it is advisable to add a certain quantity of surface active agent.

The novel catalyst molecules are prepared in such manner that these are by themselves active as surface active agents. This renders the presence of a further quantity of surface active agent optional, but in some cases such added surface active agent results in an improved yield. Due to the special design of the catalyst molecules, these result in a substantially quantitative separation of the reaction product and its phase from the catalyst system, which is in the aqueous phase. The catalyst can be used repeatedly.

The novel catalyst molecules comprise essentially three parts, namely:

a. A backbone.
b. A polar moiety.
c. A ligand moiety.

The backbone (a) may be an aliphatic chain, which may optionally contain aromatic groups and it may also contain hetero-atoms. The minimum length of the chain is about 5 atoms so as to impart the required surface active properties and in order to be active under the reaction conditions.

Amongst suitable backbones there may be mentioned moieties such as the following:

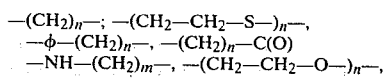

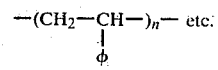

wherein $\phi$ designates a phenyl radical and n and m are integers. Such backbones may be derived from existing precursors or these may be produced by oligomerization or telomerization of suitable monomers.

The polar moiety (b) maintains the molecule in the aqueous phase. Suitable moieties are $-SO_3^-$, $-COO^-$, $N(R)_4^+$, $-PO_3H^-$, and the like. Combination of such moieties may be used. Such moieties may be attached to the backbone (a) by coupling via active groups as for example the sulfonation of an aromatic group, by chemical reaction of a suitable precursor like the saponification of a $-CCl_3$ group to obtain a $-COO^-$ group or by using it as initiating or terminating group in a polymerization reaction.

The ligand moiety (c) most frequently used in homogeneous catalysis is derived from phosphines containing either aliphatic or aromatic groups or mixtures of same. Groups like sulfones, phosphites or cyclic olefins may be used. The ligand moiety may be attached to the backbone by coupling with an active group or by using the ligand as terminating group in a polymerization reaction. Other methods for such couplings are well known in the art. Some of the ligand types suitable are as shown in the following examples of elongated moieties:

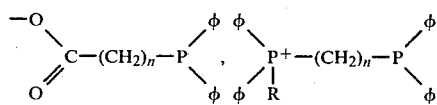

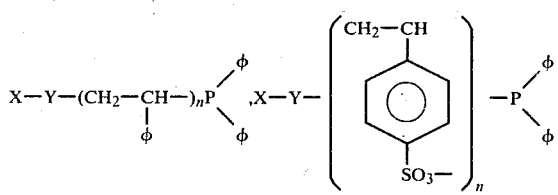

and

-continued

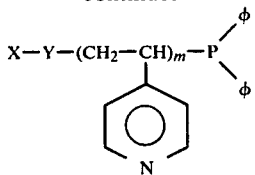

wherein φ is a phenyl group, n and m are integers, X is the polar moiety and Y is the backbone.

THE CATALYTIC REACTION

A calculated quantity of ligand is added under an inert atmosphere, such as argon, to the aqueous phase. The catalytically active metal ion is added in water soluble form or dissolved in a small quantity of organic solvent. The complex between the metal ion and the ligand is formed under agitation, whereupon the organic reaction mixture is added. The reactants may be added as such, or dissolved in a suitable organic solvent. It desired, the surfactant is added, the quantity of which is determined by experiment. Such surfactants generally increase the reaction rate, but such surfactants are optional. A milky emulsion is formed on stirring and when the reaction is terminated, stirring is stopped and the two phases are allowed to separate. Such separation may be speeded up by centrifugation or by addition of emulsion breaking agents. Addition of a small quantity of inorganic salts generally improves the rate of phase separation and in some cases this also enhances the rate of reaction proper. After phase separation is completed, the organic phase is separated and removed. This does not contain any catalysts. The organic phase may be replaced by a new quantity of organic reactants and the reaction may be repeated. No catalyst could be found in the organic phase, even by very sensitive analytical techniques.

There exists a certain degree of specificity of the surface active agent. Non-ionic surfactants may form complexes with metal ions and hinder the catalytic reaction. Certain reactions are enhanced by certain types of surfactants.

Amongst reactions which are very efficiently effected by the novel catalytic systems are hydrogenations and hydroformylations of olefins. Other forms of homogeneous catalysis may also be carried out. In the following examples catalysis was homogeneous and the solutions were transparent and showed the typical color changes of these types of reactions.

The following examples are to be construed in a non-limitative manner.

EXAMPLE 1

ω-Diphenylphosphin carboxylic acid/rhodium complex of defined chain length as hydrogenation catalyst Ethylene was telomerized according to Asscher et al., Ind.Eng. Chem.Proc.Res.Dev.2,121 (1963) to form a telomer mixture of the general formula $Cl-(CH_2)_nCCl_3$ which can be separated by fractional distillation. The $CCl_3$-group is hydrolyzed to a carboxyl group and esterified. By reacting the ω-chloro esters obtained with diphenyl phosphine potassium in THF according to Horner, Just,Lieb.Ann.Chem. (1976) 633, and by subsequent saponification there is obtained

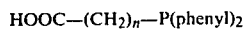

HOOC—(CH₂)ₙ—P(phenyl)₂

A weighed quantity ($12\times10^{-5}$ mole) of this ligand was dissolved in 3 ml DMSO with a quantity of $4.10^{-4}$ mole of tetra-octene dirhodium dichloride. This was dissolved in water containing a quantity of 1 g sodium dodecyl sulfate. By stirring under hydrogen and upon addition of cyclohexene the reaction was started. The results are given in the following Table.

The reaction conditions were as follows: $Rh_2Cl_2(C_8H_{14})_4$—28.3 mg. 33 ml water; 3 ml DMSO; 10 ml cyclo-hexene, T=50° C., 1 g of sodium dodecyl-sulfate, pH=7, pressure: atmospheric.

| Length of carboxylic chain, C-atoms | Ligand weight mg | Absorption of $H_2$, ml/min |
|---|---|---|
| 3 | 60.5 | 0 |
| 5 | 60 | 4.5 |
| 7 | 74.5 | 6.0 |
| 9 | 81 | 2.6 |
| 11 | 87.5 | 0.5 |

After stirring was stopped, the phases separated and the organic phase was removed. No catalyst was found in the organic phase. By adding further cyclohexene, the reaction can be repeated with similar results.

EXAMPLE 2

ω-Diphenyl phosphine carboxylic acid/Rhodium complex mixture of different chain lengths as hydrogenation catalyst The mixture of telomers of Example 1 was stripped of the 3-carbon fraction. The synthetic procedure of Example 1 was repeated giving a mixture of ω-diphenylphosphine carboxylic acids of different chain lengths. Under the conditions of Example 1 with 75 mg of mixed ligand a rate of 4 ml/minute of hydrogen was reached.

When 600 mg $NaBF_4$ was added to the reaction mixture, the rate was increased to 5.5 ml/min and the rate of phase separation after termination of the reaction was improved.

EXAMPLE 3

Hydroformylation with ω-diphenyl phosphine heptanoic acid Rh-Complex

A catalyst mixture was prepared as in example 1 for the heptanoic acid ligand, but instead of cyclohexene, 20 ml of n-octene-1 was added. The mixture was introduced in an autoclave and pressurized with 40 atm. of $H_2$ and 40 atm. of CO, heated to 80° C. and stirred magnetically. Initial pressure drop was 10 atm./hr. After 30% of reaction the autoclave was cooled down and opened. According to gas chromatographic analysis aldehydes and not alcohols were the products. As in hydrogenation the reaction could be repeated with fresh reagent and same catalyst, giving identical results.

EXAMPLE 4

Sulfonated diphenylphosphine polystyrene/Rhodium as hydrogenation catalyst

Styrene (0.7 mole) and Butyl-li (0.1 mole) were introduced into 500 ml of dry THF and reacted at −10° C., by which a living oligomer is formed. The oligomer was terminated by adding slowly at room temperature diphenylphosphine-chloride (0.1 mole) in 50 ml of dry THF. The product was precipitated by means of methanol and dried in vacuo. Molecular weight by osmotic pressure measurements in CH Cl$_3$ gave M=1330±15.

Part of the material (15 grams) was finely ground and sulfonated by heating with 150 ml of 100% H$_2$SO$_4$ at 40° C. for 45 minutes. Water (700 ml) was added and the reaction product given to settle. After decantation of the supernatant liquid pH was brought to 7 by the addition of diluted NaOH. The reaction mixture was then concentrated to 50 ml by evaporation and dried by azeotropic distillation with benzene. Benzene was removed in vacuo. The remaining sulfonated oligomer/Na$_2$ SO$_4$ mixture was separated into its components by flotation in a dibromoethane/CCl$_4$ mixture (9/11 by volume). Elemental analysis showed a degree of sulfonation of 70%. Two grams of the oligomer were dissolved in 33 ml of water together with 20 mg of RhCl$_3$.xH$_2$O 10 ml of cyclohexene added and stirred under hydrogen. Rate of hydrogen uptake was 0.5 ml/min. After the addition of 100 mg of Cetyltrimethylammoniumbromide the rate increased to 1.5 ml/min. After removal of the organic layer and the addition of a new one the same rate of hydrogenation was obtained.

EXAMPLE 5

Diphenylphosphine -vinylpyridine/styrene blockpolymer as hydrogenation catalyst

According to the methods of example 4 a living oligomer was prepared from Butyl-Li (0.1 mole) vinyl-4-pyridine (0.5 mole). Then 0.5 mole of styrene was added. The obtained living block-oligomer was terminated with 0.1 mole of diphenylphosphinechloride. The product was precipitated with petroleum ether, filtrated off and washed thoroughly with petroleum ether.

EXAMPLE 6

Comparison between sulfonated triphenylphosphine and sulfonated catalysts in hydroformylation In order to compare the superior properties of the surfactant catalysts with those of sulfonated triphenylphosphine for hydroformylation comparative runs were done at atmosferic pressure, which enabled accurate measurements to be done of the rate of gas absorption.

The reactions were performed as described for the different ligands in the respective examples 1,4 and 5 with the difference that a 1:1 CO/H$_2$ mixture was used instead of pure hydrogen and that the olefin was n-octene-1. The conditions for the sulfonated triphenylphosphine were those described in example 4. The table gives the result:

| Rates of gas absorption in ml/min of a 1:1 CO/H$_2$ mixture on hydroformylation of n-octene-1 | | | |
|---|---|---|---|
| sulfonated Tri-phenyl-phosphine | C$_7$-fraction of Example 1 | sulfonated Styrene-Oligomer of Example 4 | Pyridine Styrene Oligomer Example 5 |
| Without added surfactant 0 | does not dissolve in water | 0.02 | 0.04 |
| With 1 g of 0 | 0.2 | 0.05 | 0.07 |

| Rates of gas absorption in ml/min of a 1:1 CO/H$_2$ mixture on hydroformylation of n-octene-1 | | | |
|---|---|---|---|
| sulfonated Tri-phenyl-phosphine | C$_7$-fraction of Example 1 | sulfonated Styrene-Oligomer of Example 4 | Pyridine Styrene Oligomer Example 5 |
| SDS | | | |

P = 1 Atm.
T = 50° C.
Volume aqueous phase = 30 ml
Volume olefine = 10 ml
[Rhodium] = 2.4 · 10$^{-3}$M
[Ligand] = 7.2 · 10$^{-3}$M
SDS = Sodium Dodecyl Sulfate.

We claim:
1. A catalyst for use in homogeneous catalysis at the interface of an aqueous phase and an organic phase, said catalyst having surface active properties and including means for maintaining the catalyst in said aqueous phase, said catalyst comprising a complex of an elongated organic moiety and a metal ion, said elongated organic moiety having a structure selected from the group consisting of

$$X-Y-P\begin{matrix}\phi\\\phi\end{matrix}$$

$$X-Y-(CH_2-CH)_m-P\begin{matrix}\phi\\\phi\end{matrix}$$

(with pyridine ring attached, N)

and $$X-Y-(CH_2-CH)_n-P\begin{matrix}\phi\\\phi\end{matrix}$$

(with phenyl ring attached, SO$_3^-$)

wherein X is a polar moiety which comprises a hydrophilic group and Y is a backbone of at least 5 carbon atoms chain length, $\phi$ is a phenyl radical and m and n are integers,
the ligand moiety of said elongated organic moiety forming a complex with said metal ion and which metal ion is selected from the group consisting of rhodium, ruthenium, iridium, platinum, palladium and cobalt.

2. A catalyst in accordance with claim 1 wherein said backbone is selected from the group consisting of —(CH$_2$)n—, —(Ch$_2$—CH$_2$—S—)$_n$—,
—$\phi$—(CH$_2$)$_n$—, —(CH$_2$)$_n$—, —(CH$_2$)n—C
(O)—NH—(CH$_2$)$_m$—, —(CH$_2$—CH$_2$—O—)$_n$—,
and $$-(CH_2-\underset{\phi}{\underset{|}{CH}})_n-.$$

3. A catalyst according to claim 1, wherein said catalyst is a hydroformylation catalyst.
4. A catalyst according to claim 1, wherein the ligand moiety is a diphenyl-phosphine moiety.
5. A catalyst according to claim 1, wherein said polar moiety comprises a hydrophilic group selected from the group consisting of —SO$_3^-$, —COO$^-$, N(R)$_4^+$, and —PO$_3$H$^-$.

* * * * *